(12) United States Patent
Salamone et al.

(10) Patent No.: US 6,906,162 B2
(45) Date of Patent: Jun. 14, 2005

(54) HIGH REFRACTIVE INDEX AROMATIC-BASED SILOXANE MONOFUNCTIONAL MACROMONOMERS

(75) Inventors: Joseph C. Salamone, Boca Raton, FL (US); Jay F. Kunzler, Canadaigua, NY (US); Richard M. Ozark, Solvay, NY (US); David E. Seelye, North Chili, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/692,378

(22) Filed: Oct. 23, 2003

(65) Prior Publication Data

US 2004/0082751 A1 Apr. 29, 2004

Related U.S. Application Data

(62) Division of application No. 10/000,137, filed on Nov. 2, 2001, now Pat. No. 6,730,767.

(51) Int. Cl.$^7$ .............................................. C08G 77/00
(52) U.S. Cl. .................... 528/43; 556/437; 556/458; 528/32; 528/31; 528/37
(58) Field of Search .............................. 528/43, 32, 31, 528/37; 556/437, 458

(56) References Cited

U.S. PATENT DOCUMENTS

| 3,808,178 A | 4/1974 | Gaylord ................ 260/86.1 E |
|---|---|---|
| 3,996,187 A | 12/1976 | Travnicek .................... 260/37 |
| 3,996,189 A | 12/1976 | Travnicek .................... 260/37 |
| 4,259,467 A * | 3/1981 | Keogh et al. ................ 526/279 |
| 4,418,165 A | 11/1983 | Polmanteer et al. ......... 523/210 |
| 4,647,282 A | 3/1987 | Fedorov et al. ................ 623/4 |
| 4,737,558 A | 4/1988 | Falcetta et al. ............. 526/279 |
| 4,868,251 A | 9/1989 | Reich et al. ................. 525/479 |
| 5,336,797 A | 8/1994 | McGee et al. .............. 556/419 |
| 5,512,609 A | 4/1996 | Yang .......................... 523/107 |
| 5,623,029 A | 4/1997 | Yang .......................... 525/478 |

FOREIGN PATENT DOCUMENTS

| EP | 0492126 | 7/1992 |
| GB | 1 444 110 | 8/1976 |
| WO | WO 92/07013 | 4/1992 |
| WO | WO 97/20852 | 6/1997 |

* cited by examiner

Primary Examiner—Kuo-Liang Peng
(74) Attorney, Agent, or Firm—Toan P. Vo

(57) ABSTRACT

Optically transparent, relatively high refractive index polymeric compositions and ophthalmic devices such as intraocular lenses, corneal inlays and contact lenses made therefrom are described herein. The preferred polymeric compositions are produced through the polymerization of one or more aromatic-based siloxane macromonomers or the copolymerization of one or more aromatic-based siloxane macromonomers with one or more non-siloxy aromatic-based monomers, non-aromatic-based hydrophobic monomers or non-aromatic-based hydrophilic monomers.

4 Claims, No Drawings

HIGH REFRACTIVE INDEX AROMATIC-BASED SILOXANE MONOFUNCTIONAL MACROMONOMERS

This application is a divisional of U.S. Application Ser. No. 10/000,137 filed Nov. 2, 2001, now U.S. Pat. No. 6,730,767.

FIELD OF THE INVENTION

The present invention relates to macromonomers useful in the manufacture of biocompatible medical devices. More particularly, the present invention relates to aromatic-based siloxane monofunctional macromonomers capable of polymerization alone or copolymerization with other monomers. Upon polymerization or copolymerization, the subject macromonomers form polymeric compositions having desirable physical characteristics and refractive indices useful in the manufacture of ophthalmic devices.

BACKGROUND OF THE INVENTION

Since the 1940's ophthalmic devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants.

In general, the materials of current commercial IOLs fall into one of three general categories: silicones, hydrophilic acrylics and hydrophobic acrylics.

In general, high water content hydrophilic acrylics or "hydrogels" have relatively low refractive indices, making them less desirable than other materials with respect to minimal incision size. Low refractive index materials require a thicker IOL optic portion to achieve a given refractive power. Silicone materials may have a higher refractive index than high-water content hydrogels, but tend to unfold explosively after being placed in the eye in a folded position. Explosive unfolding can potentially damage the corneal endothelium and/or rupture the natural lens capsule and associated zonules. Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings of current polymeric materials available for use in the manufacture of ophthalmic implants, there is a need for stable, biocompatible polymeric materials having desirable physical characteristics and refractive index.

SUMMARY OF THE INVENTION

Soft, foldable, high refractive index, high elongation polymeric compositions of the present invention are produced through the polymerization of aromatic-based siloxane macromonomers, either alone or with other monomers. The subject macromonomers are synthesized through a two-phase reaction scheme. The polymeric compositions produced from the siloxane macromonomers so synthesized have ideal physical properties for the manufacture of ophthalmic devices. The polymeric compositions of the present invention are transparent, of relatively high strength for durability during surgical manipulations, of relatively high elongation, of relatively high refractive index and are biocompatible. The subject polymeric compositions are particularly well suited for use as intraocular lens (IOL) implants, contact lenses, keratoprostheses, corneal rings, corneal inlays and the like.

Preferred aromatic-based siloxane macromonomers for use in preparing the polymeric compositions of present invention have the generalized structures represented by Formula 1 and Formula 2 below,

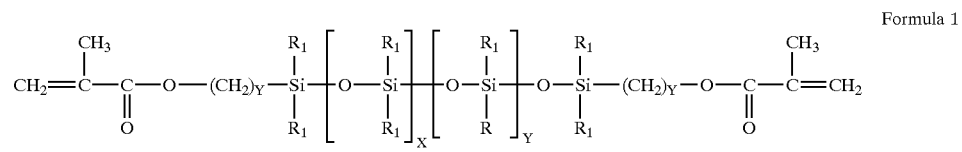

Formula 1

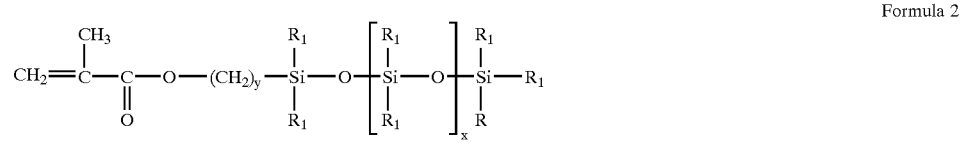

Formula 2 wherein the R groups may be the same or different aromatic-based substituents; $R_1$ is an aromatic-based substituent or an alkyl; x is a non-negative integer; and y is a natural number.

Accordingly, it is an object of the present invention to provide transparent, polymeric compositions having desirable physical characteristics for the manufacture of ophthalmic devices.

Another object of the present invention is to provide polymeric compositions of relatively high refractive index.

Another object of the present invention is to provide polymeric compositions suitable for use in the manufacture of intraocular lens implants.

Another object of the present invention is to provide polymeric compositions that are biocompatible.

Still another object of the present invention is to provide polymeric compositions that are economical to produce.

These and other objectives and advantages of the present invention, some of which are specifically described and others that are not, will become apparent from the detailed description and claims that follow.

DETAILED DESCRIPTION OF THE INVENTION

The present invention relates to novel aromatic-based siloxane macromonomers synthesized through a two-phase reaction scheme. The subject aromatic-based siloxane macreaction scheme. The subject aromatic-based siloxane macromonomers are useful in the production of biocompatible polymeric compositions. The subject polymeric compositions have particularly desirable physical properties. The subject polymeric compositions have a relatively high refractive index of approximately 1.45 or greater and a relatively high elongation of approximately 100 percent or greater. Accordingly, the subject polymeric compositions are ideal for use in the manufacture of ophthalmic devices. The aromatic-based siloxane macromonomers of the present invention are generally represented by the structures of Formula 1 and Formula 2 below:

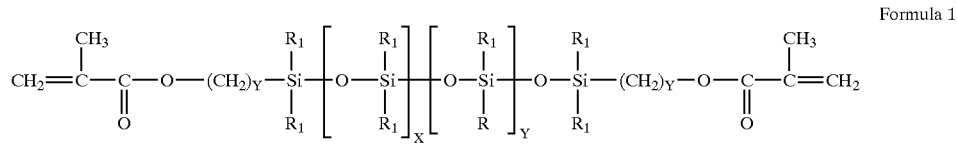

Formula 1

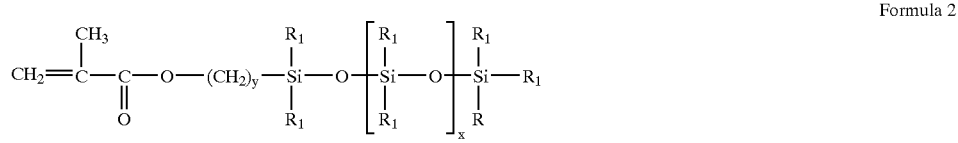

Formula 2 wherein the R groups may be the same or different $C_{6-30}$ aromatic-based substituents such as for example but not limited to

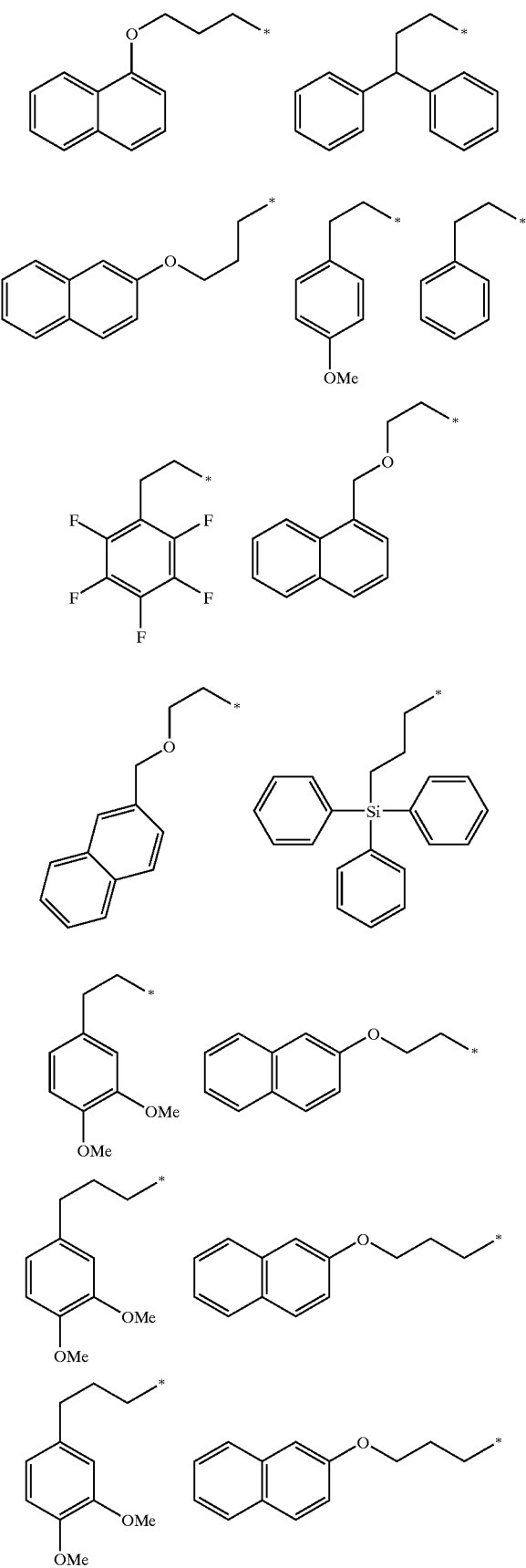

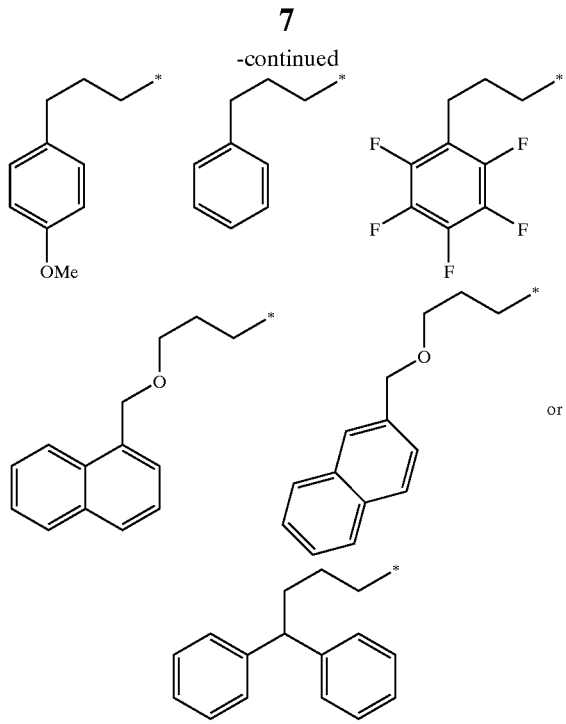

$R_1$ is a $C_{6-30}$ aromatic-based substituent as defined for R or a $C_{1-4}$ alkyl such as for example but not limited to methyl or propyl; x is a non-negative integer; and y is a natural number.

The aromatic-based siloxane macromonomers of the present invention may be synthesized through a two-phase reaction scheme. The first phase of the two-phase reaction scheme is a co-ring opening polymerization of a hydride functionalized cyclic siloxane with a methacrylate-capped disiloxane. The resultant silicone hydride-containing macromonomer is placed under high vacuum with heat to remove the unreacted silicone hydride cyclics. The second phase of the two-phase reaction scheme consists of a platinum-catalyzed hydrosilylation of an allylic functionalized aromatic with the hydride containing siloxane. The reaction is monitored for loss of hydride by both infrared (IR) and nuclear magnetic resonance (NMR) spectroscopy. NMR analysis of the final product confirms the molecular structure. In producing the subject macromonomers, a thirty percent excess of the starting allylic aromatic was used and no attempt was made to remove the same following completion of the hydrosilylation. Synthesis of the subject aromatic-based siloxane macromonomers is described is still greater detail in the examples set forth below. Additionally, specific examples of aromatic-based siloxane macromonomers of the present invention prepared in accordance with the above-described two-phase reaction scheme are set forth below in Table 1.

TABLE 1

| Side Chain (R) | Structure | Si/O Mole % | R.I. |
|---|---|---|---|
| pentafluorophenylpropyl | 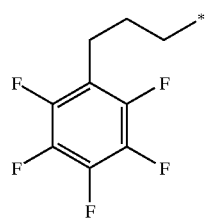 | 18/7 | 1.44 |
| phenylpropyl | 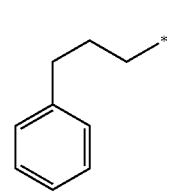 | 18/7 | 1.46 |

TABLE 1-continued

| Side Chain (R) | Structure | Si/O Mole % | R.I. |
|---|---|---|---|
| p-methoxyphenylpropyl | (p-methoxyphenylpropyl structure with OMe) | 18/7 | 1.48 |
| p-methoxyphenylpropyl | | 13/13 | 1.50 |
| p-methoxyphenylpropyl | | 7/18 | 1.52 |
| p-methoxyphenylpropyl | | 13/37 | 1.52 |
| 3,4-dimethoxyphenylpropyl | (3,4-dimethoxyphenylpropyl structure) | 18/7 | 1.48 |
| 2-naphthylpropyl ether | (2-naphthylpropyl ether structure) | 18/7 | 1.53 |
| 2-naphthylpropyl ether | | 13/13 | 1.55 |
| 2-naphthylpropyl ether | | 13/37 | 1.57 |
| diphenyldipropyl ether | (diphenyldipropyl ether structure) | 13/13 | 1.53 |
| triphenylsilylpropyl | Ph—Si(Ph)(Ph)—propyl | 13/13 | 1.58 |

The aromatic-based siloxane macromonomers of the present invention may be polymerized alone or as a copolymer with one or more aromatic non-siloxy based monomers, non-aromatic-based hydrophilic monomers, non-aromatic-based hydrophobic monomers or a combination thereof, to produce polymeric compositions of the present invention.

Examples of non-siloxy aromatic-based monomers useful for copolymerization with one or more aromatic-based siloxane macromonomers of the present invention include for example but are not limited to 2-phenyoxyethyl methacrylate, 3,3-diphenylpropyl methacrylate, 2-(1-naphthylethyl methacrylate) and 2-(2-naphthylethyl methacrylate) but preferably 2-(1-naphthylethyl methacrylate) for increased refractive index.

Examples of non-aromatic-based hydrophilic monomers useful for copolymerization with one or more aromatic-based siloxane macromonomers of the present invention include for example but are not limited to N,N-dimethylacrylamide and methyl methacrylate, but preferably N,N-dimethylacrylamide for increased hydrophilicity.

The physical and mechanical properties of copolymers produced from naphthyl side-chain siloxane macromonomers [Si(NEM)] with naphthylethyl methacrylate (NEM) and N,N-dimethylacrylamide (DMA) are set forth below in Table 2.

TABLE 2

| Composition | R.I. | Mod.(g/mm$^2$) | Tear(g/mm) | Rec. | % H$_2$O |
|---|---|---|---|---|---|
| [Si(NEM)]/ NEM/DMA | | | | | |
| 100/0/0 | 1.550 | 129 | 2 | 93 | 0 |
| 80/20/0 | 1.563 | 222 | 27 | 80 | 0 |
| 80/20/5 | | | | 74 | 1.4 |
| 80/20/10 | 1.556 | 724 | 55 | 64 | 2.7 |
| 80/20/20 | 1.536 | 357 | 31 | 77 | 6.5 |

TABLE 2-continued

| Composition | R.I. | Mod.(g/mm²) | Tear(g/mm) | Rec. | % H₂O |
|---|---|---|---|---|---|
| 85/15/0 | 1.556 | 103 | 14 | 87 | 0 |
| 85/15/10 | 1.553 | 332 | 32 | 70 | 1.7 |
| 85/15/20 | 1.533 | 289 | 18 | 81 | 8.4 |
| Commercial silicone elastomer | 1.43 | 300 | 50 | 81 | 0 |

R.I. = refractive index
Mod. = modulus
Rec. = recovery, which is a measure of the ability of a material to recover to its original shape when stretched and is measured as the percentage of recovery.

Examples of non-aromatic-based hydrophobic monomers useful for copolymerization with one or more aromatic-based siloxane macromonomers of the present invention include for example but are not limited to 2-ethylhexyl methacrylate, 3-methacryloyloxypropyldiphenylmethylsilane and 2-phenoxyethyl methacrylate but preferably 3-methacryloyloxypropyldiphenylmethylsilane for increased refractive index. The physical and mechanical properties of copolymers produced from naphthyl side chain siloxane macromonomers [Si(NEM)] with 3-methacryloyloxypropyldiphenylmethylsilane (MDPPM) and DMA are set forth below in Table 3.

TABLE 3

| Composition | R.I. | Mod.(g/mm²) | Tear(g/mm) | Rec. | % H₂O |
|---|---|---|---|---|---|
| [Si(NEM)]/ MDPPM/DMA | | | | | |
| 100/0/0 | 1.550 | 129 | 2 | 93 | 0 |
| 80/20/0 | 1.556 | 145 | 8 | 95 | 0 |
| 75/25/0 | 1.556 | 144 | 12 | 90 | 0 |
| 70/30/0 | 1.560 | 138 | 17 | 88 | 0 |
| 70/30/10 | 1.554 | 227 | 31 | 69 | 2.9 |
| 70/30/20 | 1.540 | 257 | 44 | 79 | 7.5 |
| Commercial silicone elastomer | 1.43 | 300 | 50 | 81 | 0 |

R.I. = refractive index
Mod. = modulus
Rec. = recovery, which is a measure of the ability of a material to recover to its original shape when stretched and is measured as the percentage of recovery.

No water, low water having less than 15 percent water content weight/volume (W/V) and high water "hydrogels" having 15 percent or higher water content W/V polymeric compositions of the present invention having ideal physical characteristics for ophthalmic device manufacture are described herein. Although the monofunctional siloxane macromonomers of Formula 2 polymerize or copolymerize to form crosslinked three-dimensional networks, one or more crosslinking agents may be added in quantities of preferably less than 10 percent W/V prior to polymerization or copolymerization.

Examples of suitable crosslinking agents include but are not limited to diacrylates and dimethacrylates of triethylene glycol, butyl glycol, hexane-1,6-diol, thio-diethylene glycol, ethylene glycol and neopentyl glycol, N,N'-dihydroxyethylene bisacrylamide, diallyl phthalate, triallyl cyanurate, divinylbenzene, ethylene glycol divinyl ether, N,N'-methylenebis-(meth)acrylamide, sulfonated divinylbenzene and divinylsulfone.

In order to produce polymeric compositions of the present invention from the subject monofunctional siloxane macromonomers of Formula 2, one or more strengthening agents must be used. However, strengthening agents are not necessary to produce polymeric compositions of the present invention from the subject difunctional siloxane macromonomers of Formula 1. One or more strengthening agents are preferably added in amounts less than approximately 50 percent W/V, but more preferably in amounts less than 25 percent W/V, to the macromonomers of Formula 2 prior to polymerization or copolymerization thereof.

Examples of suitable strengthening agents are described in U.S. Pat. Nos. 4,327,203, 4,355,147 and 5,270,418, each incorporated herein in its entirety by reference. Specific examples, not intended to be limiting, of such strengthening agents include cycloalkyl acrylates and methacrylates, such as for example tert-butylcyclohexyl methacrylate and isopropylcyclopentyl acrylate.

One or more suitable ultraviolet light absorbers may optionally be used in quantities typically less than 2 percent W/V in the manufacture of the subject polymeric compositions. Examples of such ultraviolet light absorbers include for example but are not limited to β-(4-benzotriazoyl-3-hydroxyphenoxy)ethyl acrylate, 4-(2-acryloyloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryloyloxyethylphenyl)-2H-benzotriazole, 2-[3'-tert-butyl-2'-hydroxy-5'-(3'-methacryloyloxypropyl)phenyl]-5-chlorobenzotriazole, 2-[3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole and 2-[3'-tert-butyl-2'-hydroxy-5'-(3"-methacryloyloxypropoxy)phenyl]-5-chlorobenzotriazole wherein β-4-benzotriazoyl-3-hydroxyphenoxy)ethyl acrylate is the preferred ultraviolet light absorber.

The subject siloxane macromonomers and polymeric compositions manufactured therefrom are described in still greater detail in the examples that follow.

EXAMPLE 1

Synthesis of Macromonomer (Two-Part Synthetic Scheme)

Part A: Methacrylate End-Capped Hydride Functionalized Macromonomer Synthesis

To a 1000 ml round bottom flask under dry nitrogen was added $D_4$ (octamethylcyclotetrasiloxane), $D_4H$ (tetramethylcyclotetrasiloxane) and $M_2$ (1,3-bis(4-methacryloyloxybutyl)tetramethyldisiloxane (molar ratio of each component dependent on desired chain length and mole % hydride substitution). Trifluoromethanesulfonic acid (0.25%) was added as initiator. The reaction mixture was stirred 24 hours with vigorous stirring at room temperature. Sodium bicarbonate was then added and the reaction mixture was again stirred for 24 hours. The resultant solution was filtered through a 0.3μ Teflon® (E.I. du Pont de Nemours and Company, Wilmington, Del.) filter. The filtered solution was vacuum stripped and placed under vacuum (>0.1 mm Hg) at 50° C. to remove the unreacted silicone cyclics. The resulting silicone hydride functionalized siloxane was a viscous, clear fluid.

Part B: General Procedure for the Synthesis of the Methacrylate End-Capped Aromatic Side-Chain Siloxanes To a 500 mL round bottom flask equipped with a magnetic stirrer and water condenser was added the methacrylate end-capped macromonomer (prepared in Part A above), the aromatic functionalized allylic ether, tetramethyldisiloxane platinum complex (2.5 mL of a 10% solution in xylenes), 75 mL of dioxane and 150 mL of anhydrous tetrahydrofuran under a nitrogen blanket. The reaction mixture was heated to 75° C. and the reaction was monitored by IR and $^1$H-NMR spectroscopy for loss of silicone hydride. The reaction was complete in 4 to 5 hours of reflux. The resulting solution was placed on a rotoevaporator to remove tetrahydrofuran and dioxane. The resultant crude product was diluted with 300 mL of a 20% methylene chloride in pentane solution and passed through a 15 gram column of silica gel using a 50% solution of methylene chloride in pentane as eluant. The collected solution was again placed on the rotoevaporator to remove solvent and the resultant clear oil was placed under vacuum (>0.1 mm Hg) at 50° C. for four hours. The resulting aromatic side-chain siloxane was a viscous, clear fluid.

EXAMPLE 2

To 80 parts of a 13/13 [Si(NEM)] macromonomer was added 20 parts of naphthylethyl methacrylate and 0.5% of Irgacure™ 819 (Ciba-Geigy, Basel, Switzerland) as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in isopropanol (IPA) for four hours, followed by air-drying and a 30 mm vacuum to remove the IPA. The clear tack-free films possessed a modulus of 222 g/mm$^2$, tear strength of 29 g/mm, recovery of 80% and a refractive index of 1.563. Commercial grade silicone rubber exhibits a modulus of 300 g/mm$^2$, a tear of 50 g/mm, recovery of 81% and a refractive index of only 1.43.

EXAMPLE 3

To 80 parts of a 13/13 [Si(NEM)] macromonomer was added 20 parts of methyl methacrylate and 0.5% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The clear tack-free films possessed a modulus of 1123 g/mm$^2$, a tear strength of 93 g/mm, recovery of 60% and a refractive index of 1.538.

EXAMPLE 4

To 80 parts of a 13/13 [Si(NEM)] macromonomer was added 20 parts of naphthylethyl methacrylate, 20 parts of N,N-dimethylacrylamide and 0.5% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The resultant film was hydrated at room temperature overnight in borate buffered saline. The clear tack-free films possessed a modulus of 357 g/mm$^2$, a tear strength of 31 g/mm, recovery of 77%, a water content of 6.5% and a refractive index of 1.536.

EXAMPLE 5

To 80 parts of a 13113 [Si(NEM)] macromonomer was added 30 parts of 3-methacryloyloxypropylmethyldiphenylsilane, 20 parts of N,N-dimethylacrylamide and 0.5% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The resultant film was hydrated at room temperature overnight in borate buffered saline. The dear tack-free films possessed a modulus of 257 g/mm$^2$, a tear strength of 44 g/mm, recovery of 79%, a water content of 7.5% and a refractive index of 1.54.

The polymeric compositions of the present invention are of relatively high refractive index, relatively high elongation and relatively high clarity. The polymeric compositions of the present invention with the desirable physical properties noted above are particularly useful in the manufacture of ophthalmic devices such as but not limited to relatively thin, foldable intraocular lens (IOL) implants and corneal inlays.

IOLs having relatively thin optic portions are critical in enabling a surgeon to minimize surgical incision size. Keeping the surgical incision size to a minimum reduces intraoperative trauma and postoperative complications. A relatively thin IOL optic portion is also critical for accommodating certain anatomical locations in the eye such as the anterior chamber and the ciliary sulcus. IOLs may be placed in the anterior chamber for increasing visual acuity in either aphakic or phakic eyes, or placed in the ciliary sulcus for increasing visual acuity in phakic eyes.

The high refractive index polymeric compositions of the present invention have the flexibility required to allow implants manufactured from the same to be folded or deformed for insertion into an eye through the smallest possible surgical incision, i.e., 3.5 mm or smaller. It is unexpected that the subject polymeric compositions could possess the ideal physical properties described herein. The ideal physical properties of the subject polymeric compositions are unexpected since high refractive index monomers typically lend to polymers that have increased crystallinity and deceased clarity, which does not hold true in the case of the subject polymeric compositions.

Ophthalmic devices such as but not limited to IOLs manufactured using the polymeric compositions of the present invention can be of any design capable of being rolled or folded for implantation through a relatively small surgical incision, i.e., 3.5 mm or less. For example, ophthalmic devices such as IOLs typically comprise an optic portion and one or more haptic portions. The optic portion reflects light onto the retina and the permanently attached haptic portions hold the optic portion in proper alignment within an eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of polymeric compositions of the present invention. Alternatively however, the IOL optic portion and haptic portions may be manufactured from one or more differing materials and/or one or more differing formulations of the polymeric compositions of the present invention, such as described in U.S. Pat. Nos. 5,217,491 and 5,326,506, each incorporated herein in its entirety by reference.

The siloxane macromonomers of the present invention may be readily cured in cast shapes, as discussed in more detail below, by one or more conventional methods. Such methods include for example but are not limited to ultraviolet light polymerization, visible light polymerization, microwave polymerization, thermal polymerization, free radical thermal polymerization or combinations thereof.

Suitable free radical thermal polymerization initiators which may be added to the monomers of the present invention include for example but are not limited to organic peroxides, such as acetyl peroxide, lauroyl peroxide, decanoyl peroxide, stearoyl peroxide, benzoyl peroxide, tert-butyl peroxypivalate, peroxydicarbonate and the like. Preferably such an initiator is employed in a concentration of approximately 0.01 to 1 percent by weight of the total monomer mixture. Representative UV initiators include those known in the field such as for example but not limited to benzoin methyl ether, benzoin ethyl ether, Darocur™ 1173, 1164, 2273, 1116, 2959, 3331 (EM Industries), Irgacur™ 651 and 184 (Ciba-Geigy, Basel, Switzerland).

Once the particular material or materials are selected for the particular ophthalmic device of choice, the same is either cast in molds of the desired shape or cast in the form of rods and lathed or machined into disks. If cast in the form of rods and lathed or machined into disks, the disks are lathed or machined into IOLs, corneal rings or the like at low temperatures below the glass transition temperature(s) of the material(s). The ophthalmic devices, whether molded or lathed/machined, are then cleaned, polished, packaged and sterilized by methods known to those skilled in the art.

In addition to intraocular lenses, the polymeric compositions of the present invention are also suitable for use in the manufacture of other ophthalmic devices such as contact lenses, keratoprostheses, capsular bag extension rings, corneal inlays, corneal rings or like devices.

IOLs manufactured using the unique polymeric compositions of the present invention are used as customary in the field of ophthalmology. For example, in a surgical procedure, an incision is placed in the cornea of an eye. Most commonly through the corneal incision the natural lens of the eye is removed (aphakic application) such as in the case of a cataractous natural lens. An IOL is then inserted into the anterior chamber, posterior chamber or lens capsule of the eye prior to closing the incision. However, the subject ophthalmic devices may be used in accordance with other surgical procedures known to those skilled in the field of ophthalmology.

While there is shown and described herein macromonomers, polymeric compositions, methods of producing the macromonomers and polymeric compositions, methods of producing ophthalmic devices using the polymeric compositions and methods of using ophthalmic devices manufactured from the polymeric compositions, all in accordance with the present invention, it will be manifest to those skilled in the art that various modifications may be made without departing from the spirit and scope of the underlying inventive concept. The present invention is likewise not intended to be limited to particular structures herein shown and described except insofar as indicated by the scope of the appended claims.

We claim:

1. A method of producing aromatic-based siloxane macromonomers

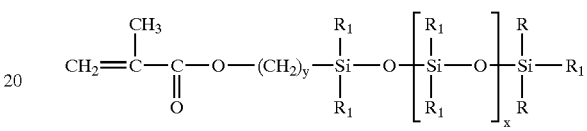

wherein the R groups may be the same or different aromatic-based substituents; $R_1$ is an aromatic-based substituent or an alkyl; x is a non-negative integer; and y is a natural number, comprising:

polymerizing a hydride functionalized cyclic siloxane with a methacrylate-capped disiloxane to form a hydride containing siloxane; and hydrosilylizing with a catalyst and an allylic-functionalized aromatic, said hydride containing siloxane.

2. The method of claim 1 wherein said R groups may be the same or different aromatic-based substituents selected from the group consisting of

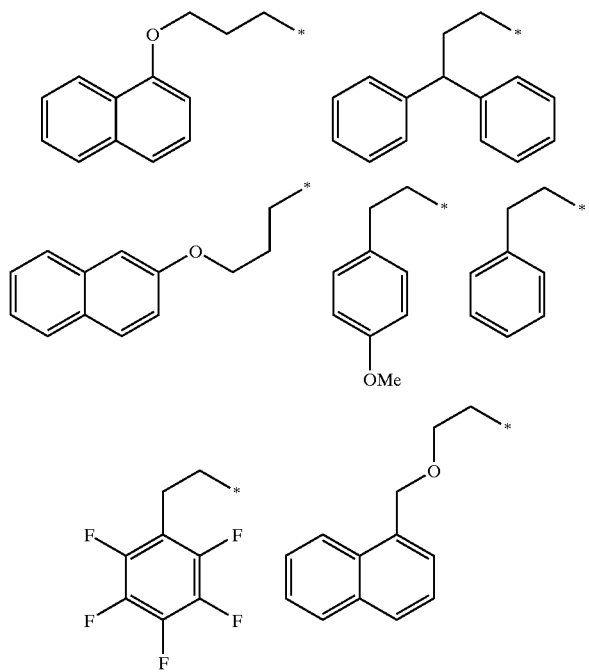

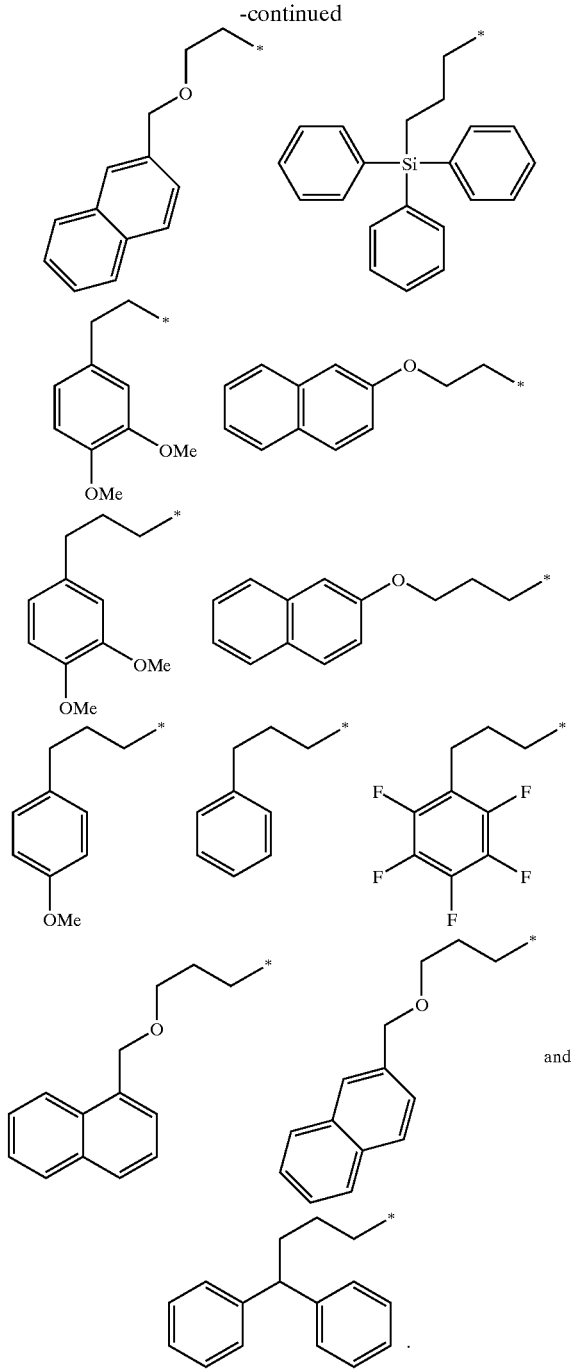
3. The method of claim 1 wherein said $R_1$ groups may be the same or different aromatic-based substituents or alkyl substituents.
4. The method of claim 1 wherein said $R_1$ groups may be the same or different $C_{6-30}$ aromatic-based substituents or $C_{1-4}$ alkyl substituents.
* * * * *